United States Patent
Henderson et al.

(10) Patent No.: US 6,487,430 B1
(45) Date of Patent: *Nov. 26, 2002

(54) ELECTRODE CONNECTOR

(75) Inventors: Robert E. Henderson, West Bend, WI (US); Teresa Guichard, Cordova, TN (US)

(73) Assignee: GE Medical Systems Information Technologies, Inc., Waukesha, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/502,978

(22) Filed: Feb. 11, 2000

Related U.S. Application Data

(60) Provisional application No. 60/119,677, filed on Feb. 11, 1999.

(51) Int. Cl.⁷ .................................. A61B 5/04
(52) U.S. Cl. ...................... 600/394; 439/909
(58) Field of Search ................................ 600/372, 373, 600/394; 439/909

(56) References Cited

U.S. PATENT DOCUMENTS

| | | | | |
|---|---|---|---|---|
| 1,086,820 A | * | 2/1914 | Hammond | 439/909 |
| 1,291,297 A | * | 1/1919 | Walas | 439/909 |
| 1,651,294 A | * | 11/1927 | Rumore | 439/909 |
| 3,740,703 A | * | 6/1973 | Sessions | 439/909 |
| 4,200,348 A | * | 4/1980 | Stupay | 439/909 |
| 4,206,960 A | * | 6/1980 | Tantillo et al. | 439/909 |
| 4,220,387 A | * | 9/1980 | Biche et al. | 439/909 |
| 4,303,293 A | | 12/1981 | Grunwald | |
| 4,390,223 A | * | 6/1983 | Zenkich | 439/909 |
| 4,674,817 A | * | 6/1987 | Olms | 439/909 |
| 5,355,883 A | | 10/1994 | Ascher | |
| 5,624,281 A | | 4/1997 | Christensson | |
| 5,626,135 A | | 5/1997 | Sanfilippo | |
| 5,944,562 A | | 8/1999 | Christensson | |
| 6,357,089 B1 | | 3/2002 | Koguchi et al. | |

* cited by examiner

*Primary Examiner*—Linda C. M. Dvorak
*Assistant Examiner*—David M. Ruddy
(74) *Attorney, Agent, or Firm*—Michael Best & Friedrich LLP

(57) ABSTRACT

An apparatus and method to connect to an electrode is claimed. The apparatus includes a first mating member and a second mating member having first and second openings. A resilient body portion connects the first and second mating members.

31 Claims, 4 Drawing Sheets

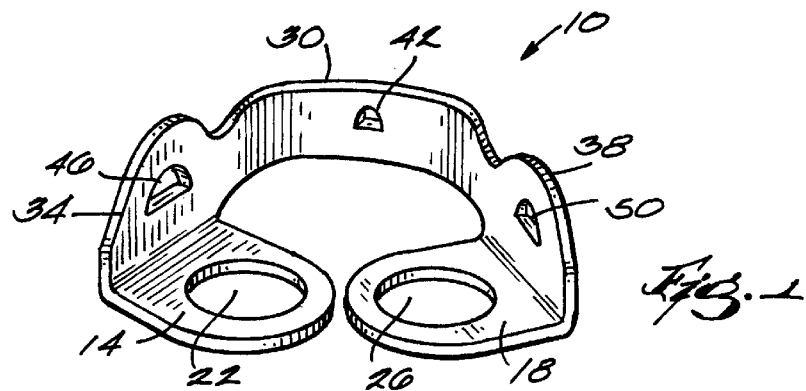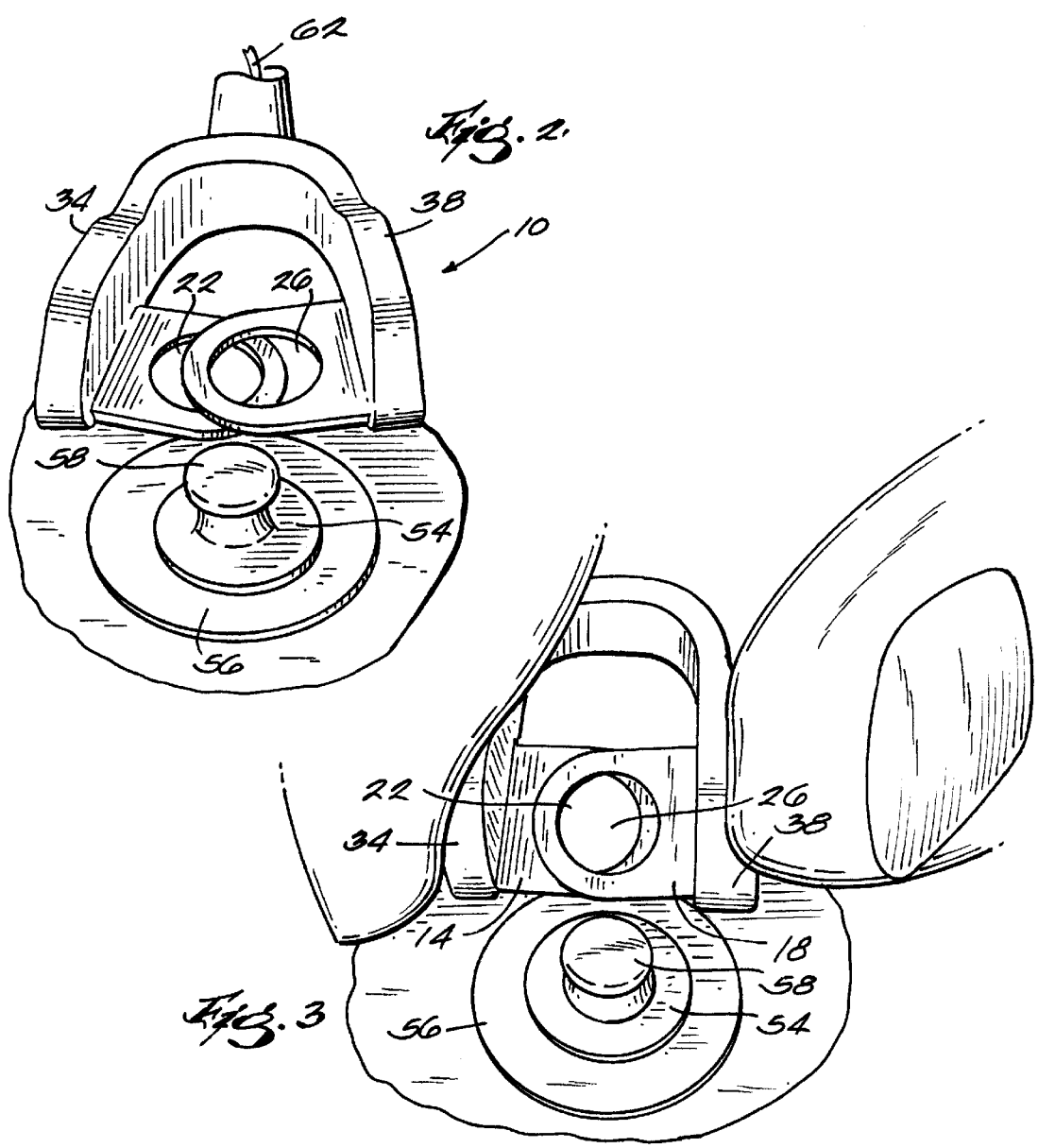

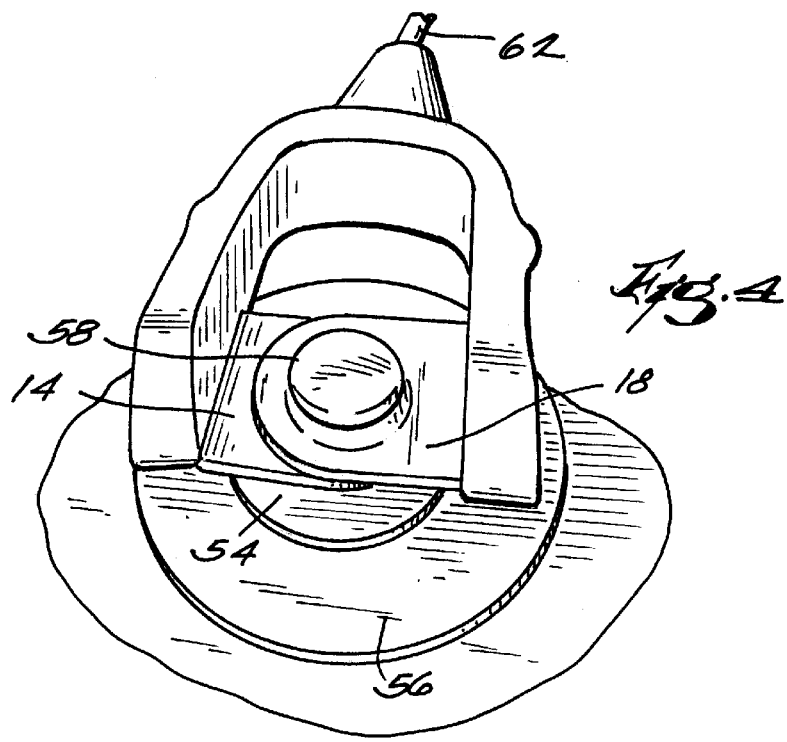
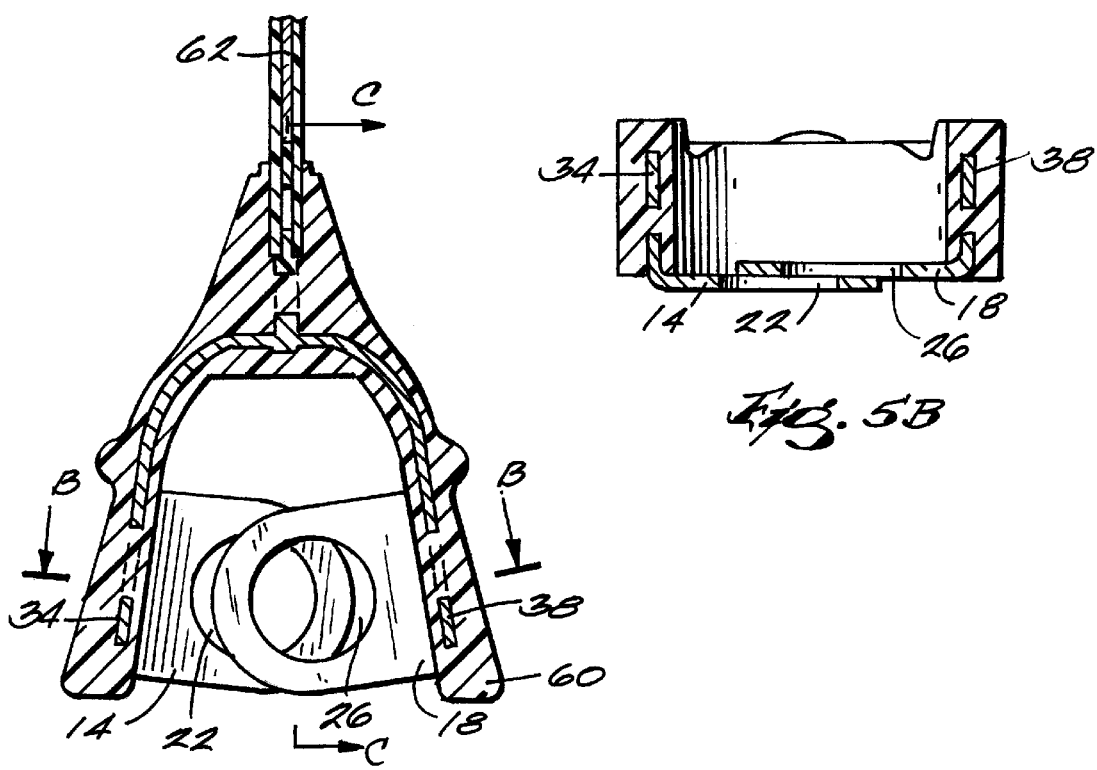

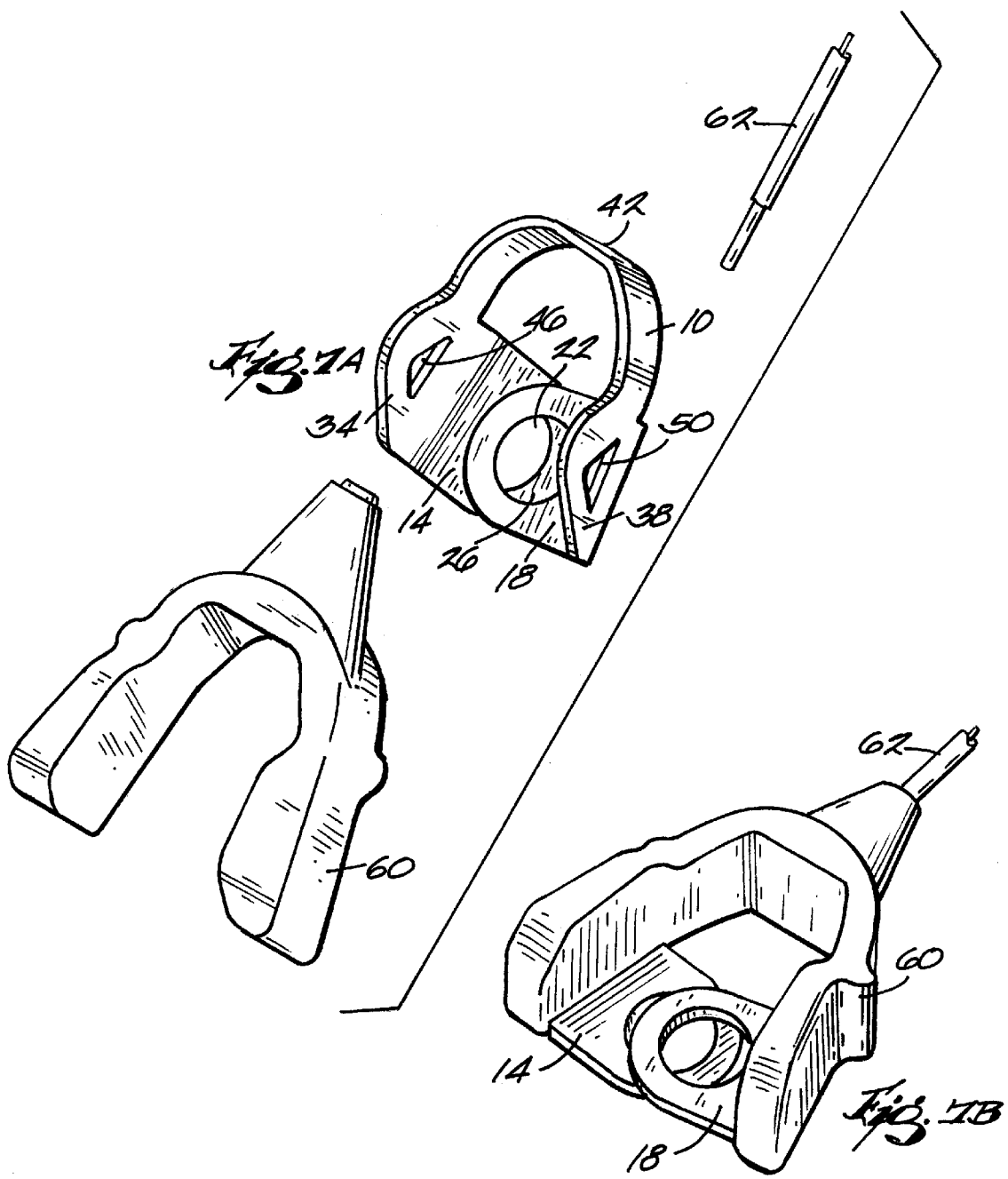

| DATE | S/N | CONTACT RESISTANCE (IN OHMS) |
|---|---|---|
| 4/8/97 | J-1904 | 0.05 |
| 4/8/97 | J-1905 | 0.06 |
| 4/8/97 | J-1906 | 0.06 |
| 4/8/97 | J-1907 | 0.06 |
| 4/8/97 | J-1908 | 0.05 |

Fig. 8A

Prior Art

| DATE | S/N | CONTACT RESISTANCE (IN OHMS) |
|---|---|---|
| 4/8/97 | J-1909 | 0.11 |
| 4/8/97 | J-1910 | 0.11 |
| 4/8/97 | J-1911 | 0.11 |
| 4/8/97 | J-1912 | 0.11 |
| 4/8/97 | J-1913 | 0.13 |

Fig. 8B

ELECTRODE CONNECTOR

CROSS-REFERENCE TO RELATED APPLICATIONS

This application claims priority under 35 U.S.C. § 119 of prior filed, co-pending provisional application No. 60/119,677 filed Feb. 11, 1999, and hereby incorporates that disclosure by reference.

BACKGROUND OF THE INVENTION

The invention relates to an apparatus that can be connected to an electrode on a patient, and a method of connecting a device to an electrode on a patient. More particularly, the invention relates to an apparatus and method for providing an electrode connector having a low profile and low contact resistance.

Electrical treatment and diagnostic techniques are well established in the medical field. For example, it has become well recognized that electrical impulses can be employed for desired medical therapeutic and physical rehabilitative purposes. Further, critical care monitoring of infants and other patients requiring constant care frequently involve electrode based monitoring of electrophysiological signals.

Numerous electrode configurations have been described in the prior art. Typical configurations frequently encountered in acute care of premature infants include use of a garment-type snap, or use of a grabber, which operates like a clothespin. A problem encountered with using garment-type snaps is that snaps tend to disconnect easily. A problem encountered with grabbers is that grabbers do not have a low profile, a feature particularly desirable in dealing with infants. Further, traditional snaps and grabbers often have high contact resistance, leading to poor electrical conductivity.

SUMMARY OF THE INVENTION

Accordingly, the invention provides an apparatus and method to provide a reliable, low profile connection to patient electrodes. The invention allows an apparatus to be connected to an electrode attached to a patient. The apparatus has first and second mating members shaped to form first and second openings. The first and second mating members lie on planes substantially parallel to one another. The apparatus also includes a body portion connecting the first and second mating members. The body portion is integrally formed with the first and second mating members, and has a low profile allowing the connector to be particularly desirable for neonatal patients. When the body portion is compressed, the first and second openings are substantially aligned. The body portion may further include an opening allowing a lead wire to be electrically connected to the body portion.

It is an advantage of the invention to provide a method and apparatus to provide reliable electrical and mechanical connections to electrodes.

It is another advantage of the invention to provide a method and apparatus of providing a low profile connection to electrodes.

It is another advantage of the invention to provide a connector for electrodes having low contact resistance.

It is another advantage of the invention to provide a connector for electrodes that is lightweight.

It is another advantage of the invention to provide a method and apparatus for providing a connector to electrodes having a large contact surface.

Other features and advantages of the invention are set forth in the following drawings, detailed description and claims.

BRIEF DESCRIPTION OF THE DRAWINGS

FIG. 1 is a perspective view of the connector device embodying the invention.

FIG. 2 is a perspective view of the connector device in a relaxed position and adjacent a mating stud attached to an electrode on a patient.

FIG. 3 shows a top view of the connector device in a compressed position adjacent the mating electrode.

FIG. 5A is a section view of a connector device.

FIG. 5B is a side view of the connector device of FIG. 5A along section line B—B.

FIG. 6 is a side view of the connector device shown in FIG. 6 along section line C—C.

FIG. 7A is an exploded, unassembled view of the connector device and a shell for a connector device.

FIG. 7B is a perspective view of the connector device and a shell in an assembled position.

FIG. 8A is a chart illustrating the contact resistance of the connector device embodying the invention.

FIG. 8B is a chart illustrating the contact resistance of prior art electrode connectors.

DETAILED DESCRIPTION OF THE PREFERRED EMBODIMENT

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also it is to be understood that the phraseology and terminology used herein is for the purposes of description and should not be regarded as limiting.

FIG. 1 illustrates a connector device 10 embodying the invention, or more particularly, a raw metal connector before being overmolded with a plastic shell 60, which will be discussed below. The connector device 10 is formed from a single piece of electrically conductive metal. In a preferred embodiment, the metal is nickel-plated stainless steel.

The connector device 10 includes a first mating member 14 and a second mating member 18 arcuately shaped to form first and second openings 22 and 26, respectively. The first and second mating members 14 and 18 are connected by a resilient or flexible body portion 30, and positioned in substantially parallel planes. In the preferred embodiment, as shown in FIG. 6, the thickness of first and second mating members 14 and 18 is approximately 0.015 inches.

The body portion 30 of the device 10 includes first and second side ridged portions 34 and 38 and center portion 40 connecting side ridged portions 34 and 38. The center portion 40 and side ridged portions 34 and 38 are generally perpendicular to the first and second mating members 14 and 18. First and second side ridged portions 34 and 38 are arcuately shaped to form first and second side openings 46 and 50. The body portion 30 also includes a center opening 42, from which a lead wire may be attached.

The body portion 30, side portions 34 and 38 and the center portion 40 each have a height. In a preferred embodiment, the height of the side portions 34 and 38 is greater than the height of the body portion 30. This allows a user of the device 10 to easily compress the side portions 34 and 38 together, towards one another. In a preferred embodiment, the height of the body portion 30 is less than about 0.175 inches, and preferably about 0.167 inches, which gives the device 10 a low profile. Minimizing the size of the connector device 10 decreases the total weight of the connector device 10. In a preferred embodiment, the weight of the connector device 10 is less than about 0.0286 ounces, and preferably about 0.0282 ounces. Minimizing the height profile and weight of the connector device 10 is particularly desirable for neonatal electrodes.

In a preferred embodiment, an insulating shell 60 can be molded over the connector device 10 as shown in FIG. 7A and 7B. The shell 60, preferably a plastic such as polypropylene, is molded onto the connector device 10 such that the electrode wire 62 protrudes through the center opening 42. In a preferred embodiment, the electrode wire 62 is soldered onto the connector device 10 through the center opening 42.

FIG. 2 shows the device 10, insulated by the shell 60. In FIG. 2, the device 10 is proximate, but not attached, to a mating electrode stud 54 that is electrically connected and attached to an electrode 56 on a patient. The electrode stud 54 has a protruding portion 58 integrally formed with the body of the electrode stud 54.

The connector device 10 is shown in the relaxed position in FIG. 2, wherein the first and second mating members 14 and 18 only partially overlap, and the first and second openings 22 and 26 only partially align. The connector device 10 is biased towards the relaxed position. In the relaxed position, the partial alignment of the openings 22 and 26 does not allow the device 10 to be placed over the electrode stud 54.

When the first and second side portions 34 and 38 are compressed together, as shown in FIG. 3, the first and second side mating members 14 and 18 substantially completely overlap, and the first and second openings 22 and 26 are substantially aligned. Approximately 2.3 pounds of force is necessary to position the device in the compressed position. In a preferred embodiment, the distance between the first and second mating members 14 and 18 is approximately 0.003 millimeters when the connector device is in the compressed position. When the openings 22 and 26 are substantially aligned, the device 10 can be positioned over the protruding portion 58 of the electrode stud 54. Once the device 10 is placed over the electrode stud 54, and the protruding portion 58 is situated within the openings 22 and 26 the ridged side portions 34 and 38 are released, and the bias forced connector device 10 causes side portions 34 and 38 to move away from one another into the relaxed position. As a result, the first and second mating members 14 and 18, and the openings 22 and 26 located therein, engage the protruding portion 58 of the electrode stud 54, thereby attaching the device 10 to the electrode stud 54 as shown in FIG. 4.

When the connector device 10 is attached to the electrode stud 54, an electrical connection is made such that the patient's physiological signals may be monitored. A lead wire 62 can be inserted into the center opening 42 of the connector device 10 to transfer electrical signals captured by the electrode via the electrode stud 54 and connector device 10 to a monitor (not shown). In a preferred embodiment, the lead wire 62 is soldered onto the connector device 10 through the center opening 42.

Because the connector device 10 is biased toward the open, relaxed position, pull action is not required to open or remove the connector device 10 from the protruding portion 58 of the electrode stud 54. Instead, to remove the attached connector device 10, the ridged side portions 34 and 38 must again be compressed to release the tension created by the engagement of the mating members 14 and 18 with the electrode stud 54 when the device 10 is attached to the electrode stud 54.

FIG. 8A illustrates the contact resistance of the invention. FIG. 9B is a chart illustrating the contact resistance of prior art electrode connectors. As indicated, the contact resistance of the invention is lower than that of prior art connectors. Accordingly, the connector device 10 of the invention maintains better electrical contact than prior art connectors. The contact resistance of the connector of the invention is preferably less than about 0.010 ohms. In a preferred embodiment, the contact resistance is approximately 0.05 ohms.

Various other features and advantages of the invention are set forth in the following claims.

What is claimed is:

1. An electrode connector for attachment to an electrode stud of an electrode, the electrode connector comprising:
   a first mating member defining a through opening therein adapted to receive the electrode stud;
   a second mating member defining a through opening therein adapted to receive the electrode stud; and
   a resilient member connected between the first and second mating members and biasing the first and second members away from each other to a rest position, the resilient member having a first side portion, a second side portion and a center portion connecting the first and second side portions,
   the first side portion, second side portion and the center portion each having a height, and the height of the first side portion and the height of the second side portion being greater than the height of the center portion.

2. The electrode connector of claim 1, wherein the first and second mating members are movable against the biasing force to a second position such that the respective openings are sufficiently aligned to allow insertion of the electrode stud through both openings so that releasing the first and second mating members causes the mating members to move from the second position to a third portion releasably securing the first and second mating members to the electrode stud.

3. The electrode connector of claim 2, wherein at least a portion of the first or second mating member engages the electrode stud in the third position.

4. The electrode connector of claim 2, wherein no pull action is required to move the electrode connector from the rest position to the second position.

5. The electrode connector of claim 2, wherein no pull action is required to remove the connector from the stud when the connector is in the third position.

6. The electrode connector of claim 1, wherein the openings of the first mating member and the second mating member are not aligned in the rest position.

7. The electrode connector of claim 1, each side portion extends perpendicularly from the first mating member and the second mating member.

8. The electrode connector of claim 1, wherein the resilient body has a center portion including an opening for attaching a lead wire thereto.

9. The electrode connector of claim 1, wherein the connector is at least partially covered by a plastic cover.

10. The electrode connector of claim 1, wherein the opening of the first mating member has a first diameter and the opening of the second mating member has a second diameter, the diameters being substantially equal.

11. The electrode connector of claim 1, wherein the first member lies in a first plane, the second member lies in a second plane, and the first plane and second plane are substantially parallel.

12. The connector of claim 1, wherein the first and second mating members form an angle in a rest position, and the angle is about 15 to about 52 degrees.

13. The connector of claim 1, wherein the resilient member is semi-circular.

14. The connector of claim 1, wherein the connector provides a contact resistance of less than about 0.010 ohms.

15. An electrode connector for attachment to an electrode stud of an electrode, the electrode connector comprising:
   a first mating member defining an opening adapted to receive the electrode stud, the first mating member lying in a first plane;
   a second mating member defining an opening adapted to receive the electrode stud, the second mating member lying in a second plane; and
   a resilient member connected between the first and second mating member and biasing the first and second members away from each other to a rest position wherein the first and second mating members do not overlap, and
   wherein the planes of the first and second members are substantially parallel, thereby allowing the first and second mating members to overlap one another when the mating members are moved toward one another against the biasing force, the first mating member, second mating member and resilient member being integral.

16. The electrode connector of claim 15, wherein the first and second mating members are movable against the biasing force to a second position such that the respective openings are sufficiently aligned to allow insertion of the electrode stud through both openings so that releasing the first and second mating members causes the mating members to move from the second position to a third portion releasably securing the first and second mating members to the electrode stud.

17. The electrode connector of claim 16, wherein at least a portion of each of the first and second mating members engages the electrode stud in the third position.

18. The electrode connector of claim 16, wherein no pull action is required to move the electrode connector from the rest position to the second position.

19. The electrode connector of claim 16, wherein no pull action is required to remove the connector from the stud when the connector is in the third position.

20. The electrode connector of claim 15, wherein the openings of the first mating member and the second mating member are not aligned in the rest position.

21. The electrode connector of claim 15, wherein the resilient body includes first and second ridged portions having respective heights.

22. The electrode connector of claim 15, wherein the resilient body has a center portion including an opening for attaching a lead wire thereto.

23. The electrode connector of claim 15, and further comprising a molded plastic body at least partially covering at least a one of the first mating member, second mating member and resilient member.

24. The electrode connector of claim 15, wherein the opening of the first mating member has a first diameter and the opening of the second mating member has a second diameter, the diameters being substantially equal.

25. The connector of claim 15, wherein the first and second mating members form an angle in the rest position, and the angle is about 15 to about 52 degrees.

26. The connector of claim 15, wherein the resilient member is semi-circular.

27. The connector of claim 15, wherein the connector provides a contact resistance of less than about 0.010 ohms.

28. A method of attaching a lead wire for a patient monitor to a patient, the method comprising:
   placing an electrode having an electrode stud on a patient;
   providing a connector electrically connected to a lead wire, the connector having a first mating member defining an opening adapted to receive the electrode stud, a second mating member defining an opening adapted to receive the electrode stud, and a resilient member connected between the first and second mating members and biasing the first and second members away from each other to a rest position, the resilient member having a first side portion, a second side portion and a center portion connecting the first and second side portions,
   the first side portion, second side portion and the center portion each having a height, and the height of the first side portion and the height of the second side portion being greater than the height of the center portion;
   compressing the first and second mating members against the biasing force to a second position, wherein the first and second openings are aligned sufficiently to allow the electrode stud to extend therethrough;
   placing the connector over the electrode stud such that the electrode stud extends through the first and second openings; and
   releasing the connector device such that the first and second mating members move away from one another to a third position wherein at least a portion of the first or second mating member engages the stud.

29. The method of claim 28, wherein no pull action is required to compress the first and second mating members against the biasing force to move the connector from the rest position to the second position.

30. The method of claim 28, wherein no pull action is required to move the connector from the third position, thereby removing the connector from the stud.

31. The method of claim 28, wherein the openings are at least partially aligned in the rest position.

* * * * *

UNITED STATES PATENT AND TRADEMARK OFFICE
CERTIFICATE OF CORRECTION

PATENT NO.    : 6,487,430 B1  
DATED         : November 26, 2002  
INVENTOR(S)   : Robert E. Henderson and Teresa Guichard It is certified that error appears in the above-identified patent and that said Letters Patent is hereby corrected as shown below:

<u>Column 2,</u>  
Line 13, add:  
-- FIG. 4 shows the connector device connected to the electrode stud. --

Signed and Sealed this

Seventeenth Day of June, 2003

JAMES E. ROGAN  
*Director of the United States Patent and Trademark Office*